United States Patent
Ali

(10) Patent No.: US 10,568,915 B1
(45) Date of Patent: Feb. 25, 2020

(54) METHOD OF PREPARING A THERAPEUTIC COMPOSITION USING A PREPARATION FROM EPIDERMAL GEL SECRETIONS OF CATFISH

(71) Applicant: Jassim M. Hassan M. Ali, Safat (KW)

(72) Inventor: Jassim M. Hassan M. Ali, Safat (KW)

( * ) Notice: Subject to any disclaimer, the term of this patent is extended or adjusted under 35 U.S.C. 154(b) by 0 days.

(21) Appl. No.: 16/293,094

(22) Filed: Mar. 5, 2019

(51) Int. Cl.
*A61K 35/60* (2006.01)
*A61K 9/19* (2006.01)

(52) U.S. Cl.
CPC ............... *A61K 35/60* (2013.01); *A61K 9/19* (2013.01)

(58) Field of Classification Search
None
See application file for complete search history.

(56) References Cited

U.S. PATENT DOCUMENTS

| | | | |
|---|---|---|---|
| 5,658,594 A | 8/1997 | Al-Hassan | |
| 5,912,018 A * | 6/1999 | Al-Hassan | A61K 35/60 424/520 |
| 8,551,532 B2 * | 10/2013 | Al-Hassan | A61K 35/60 424/520 |

OTHER PUBLICATIONS

Al-Hassan et al. "Catfish epidermal secretions in response to threat or injury," Marine Biology, 88, 117-123 (1985) (Year: 1985).*

Al-Hassan et al. Comparative Biochemistry and Physiology Part B: Comparative Biochemistry vol. 88, Issue 3, 1987, pp. 813-822 (Year: 1987).*

Thomson et al. "Purification of a Toxic Factor From Arabian Gulf Catfish Epidermal Secretions," Toxicon, 36, 859-866, (1998) (Year: 1998).*

Al-Hassan et al. "Vasoconstrictor Components in the Arabian Gulf Catfish (*Arius thalassinus*, Ruppell) Proteinaceous Skin Secretion," Toxicon, 24, pp. 1009-1014 (1986) (Year: 1986).*

Al-Hassan et al., "Skin Preparations from Catfish (*Arius bilineatus*, Val.) Contain a Lipid Which Inhibits Cancer Cell Survival In Vitro," The FASEB Journal, vol. 30, No. 1 supplement, Apr. 1, 2016.

Yang et al., "Abstract 2246: Anti-proliferative activities of lipid fraction of extract from the skin of the catfish Arius Bilineatus, Valenciennes," AACR Annual Meeting 2017; Apr. 1-5, 2017; Washington, DC.

Yang et al., "Anti-proliferative and anti-invasiveness of the lipid fraction of the skin extract from the catfish Arius bilineatus, valenciennes in human pancreatic cancer is associated with regulation of lipid metabolism," Cancer Research 77, (13 Supplement):2246-2246, Jul. 2017.

* cited by examiner

*Primary Examiner* — Christina Bradley
(74) *Attorney, Agent, or Firm* — Richard C. Litman; Nath, Goldberg & Meyer

(57) ABSTRACT

A method of preparing a therapeutic composition from the epidermal gelatinous secretion of catfish includes mixing catfish epidermal gel secretions (EGS) with phosphate buffered saline (pH 7.5) to provide an extract, homogenizing the extract to provide a homogenized extract, and centrifuging the homogenized extract to provide a soluble protein fraction and an insoluble protein fraction. The therapeutic composition can include about 87% soluble proteins and about 13% lipids.

1 Claim, No Drawings

METHOD OF PREPARING A THERAPEUTIC COMPOSITION USING A PREPARATION FROM EPIDERMAL GEL SECRETIONS OF CATFISH

BACKGROUND

1. Field

The disclosure of the present patent application relates to a therapeutic composition, and particularly, to a method of preparing a therapeutic composition from the epidermal gel secretions of catfish.

2. Description of the Related Art

The Arabian Gulf catfish (*Arius bilineatus* (Valenciennes)) naturally exudes a proteinaceous gel-like material ("epidermal gel secretion" or "EGS") from its epidermis upon stress or injury. The epidermal gel secretion includes a complex mixture of biochemically and pharmacologically active components, such as soluble proteins, lipids, and insoluble proteins.

The epidermal gel secretion can provide numerous therapeutic benefits. Often times, however, the Arabian Gulf catfish produces venoms from its venomous spines and venom glands near its pectoral spines which mix with secretions on the catfish skin. Additionally, since the gelatinous secretion is exuded while the catfish is still alive, contaminants other than the venom (such as feces, vomit and blood) are also often mixed with the epidermal secretion. Thus, a method of preparing a therapeutic composition from the epidermal gelatinous secretion of catfish solving the aforementioned problems is desired.

SUMMARY

A method of preparing a therapeutic composition using the epidermal gel secretion of catfish includes collecting the epidermal gel secretion of catfish and fractionating the epidermal gel secretion to obtain a soluble protein fraction. The soluble protein fraction can include about 87% soluble proteins and about 13% lipids. The therapeutic composition can include the soluble protein fraction including about 87% soluble proteins and about 13% lipids.

Fractionating the epidermal gel secretion of catfish can include mixing the catfish epidermal gel secretions with phosphate buffered saline to provide an extract, homogenizing the extract to provide a homogenized extract, and centrifuging the homogenized extract to provide a soluble protein fraction and an insoluble protein fraction. The soluble fraction can be freeze dried to provide a powdered soluble fraction. If desired, the insoluble protein fraction can be fractionated (in the manner described above for fractionating the EGS) to separate any undissolved soluble proteins therefrom. The additional soluble protein fraction extracted from the insoluble protein fraction can be added to the original soluble protein fraction to enrich the original soluble protein fraction.

The freeze-dried soluble fraction can be analyzed to determine a ratio of the concentration of soluble protein to lipids. Generally, it can be expected that the freeze-dried powdered soluble fraction includes about 87% soluble proteins. If the freeze-dried powdered soluble fraction includes less than about 13% lipids, however, the soluble fraction can be supplemented with lipids from an additional lipid fraction to provide a soluble protein fraction having about 87% soluble proteins and about 13% lipids. The additional lipid fraction can be obtained from the freeze-dried EGS. The therapeutic composition can include the soluble protein fraction having about 87% soluble proteins and about 13% lipids.

For administration of the composition, the soluble protein fraction can be taken out of deep freeze (−80° C.), dissolved in saline in phosphate buffer (pH 7.5), and maintained at temperatures ranging from about 4° C. to about 6° C. to be ready for administration. In an embodiment, the soluble protein fraction is dissolved in phosphate buffer saline for administration. In an embodiment, the composition includes the soluble protein fraction and the phosphate buffer saline. It is preferable to dissolve the soluble protein fraction and administer the composition when the composition is still cold, e.g., temperatures ranging from about 4° C. to about 6° C. For example, the composition can be maintained in crushed ice or in a refrigerator until it is ready to be administered.

These and other features of the present disclosure will become readily apparent upon further review of the following specification.

DETAILED DESCRIPTION OF THE PREFERRED EMBODIMENTS

A method of preparing a therapeutic composition from the epidermal gelatinous secretion of catfish can include collecting epidermal gel secretions (EGS) from the catfish and fractionating the epidermal gel secretions to obtain a soluble protein fraction comprising about 87% soluble proteins and about 13% lipids. The therapeutic composition includes the soluble protein fraction comprising about 87% soluble proteins and about 13% lipids.

The soluble protein fractions described herein can be obtained from the epidermal gel secretions (EGS) of Arabian Gulf catfish, such as (*Arius bilineatus* (Valenciennes)). The Arabian Gulf catfish naturally exudes a gelatinous secretion through its skin after the catfish is shocked, e.g., threatened or injured. For example, once a catfish is caught, it will struggle as it is towed to the surface with the fishing hook still in its mouth (as the catfish is a bottom dweller). As the fish reaches the surface, it struggles to defend itself and to escape the reduction in water pressure. This will cause the fish to secrete the EGS along with one or more contaminants, such as venom from its venom glands, faeces from its anal pore, vomit from its mouth and through its gills, and blood through its gills if the fishing hook catches the gill rays. Shocking the fish can also be accomplished by thermal shock, physical abrasions, or neural stimulation. The fish can be washed one or more times to remove contaminants. While the fish is still alive, the fish can be held through its gills to induce production of additional EGS. The EGS without any remaining contaminants on the skin can be collected by a gentle mechanical scraping or suction of the skin. Preferably, the EGS is immediately frozen, e.g., in dry ice, then cooled to −80° C. (deep freeze) or kept frozen in liquid nitrogen, to limit microbial growth and prevent biochemical decomposition.

The soluble protein fractions described herein can include a mixture of highly active biochemical and pharmacological components. These include, for example, a plasma clotting factor that has been found to be specific to blood clotting factor X1, a hemolytic factor, platelet activating factors (PAFs) at unusually high levels (more than 5,000 times the threshold level required for normal platelet activation), and a hemagglutination factor. The soluble fraction can also include vaso-active components, phosphatases, including an acid phosphatase, a general esterase and a tyrosine specific esterase, and proteins with collagenase-like activities that cleave collagen into fragments. The soluble fraction can include a factor that activates phospholipase $A_2$, tyrosine and serine/threonine protein phosphorylase, proteolytic and antimicrobial activities, leukotrienes, interleukin 1 and growth factors that affect macrophages and pancreatic β-cells, along with four protein components that are capable of binding human fibronectin. The lipids in the soluble fraction can include neutral lipids, phospholipids, and glycolipids. For example, the neutral lipids can include eicosanoids, cholesterol, triglycerides, fatty acids and steroids.

It should be understood that a therapeutic composition can be prepared from epidermal gel secretions of other species of catfish or any other aquatic or terrestrial creature (e.g., moray eels, slugs, and worms) that produces epidermal gel secretions having biologically active components similar to those present in the soluble protein fractions described herein.

As used herein, the term "about," when used to modify a numerical value, means within ten percent of that numerical value.

According to an embodiment, the method of preparing a therapeutic composition from the epidermal gelatinous secretion of catfish can include collecting epidermal gel secretions (EGS) from the skin of Arabian Gulf catfish (*Arius bilinealus* (Valenciennes)) and fractionating the EGS to provide a soluble protein fraction (SPF).

In an embodiment, the soluble protein fraction (SPF) can be extracted from the EGS by thawing the frozen EGS to a temperature ranging from about 4° C. to about 6° C. and mixing the thawed EGS with a suitable, non-toxic extraction buffer (e.g., saline in phosphate buffer at pH 7.5) to provide an extract. This step and all subsequent purification procedures can be carried out at about 4° C. to about 6° C. in the dark, unless otherwise indicated. The extraction buffer should not denature or affect the proteins in the EGS in any way. Preferably, the extraction buffer includes phosphate buffered saline having 0.05M ($NaH_2PO_4Na_2HPO_4$) and 0.14M NaCl, pH 7.5. The thawed EGS can be mixed with an equal volume of the extraction buffer and homogenized, e.g., with an Ultra Truex (IKA) homogenizer. The homogenized extract can then be centrifuged to provide a soluble protein fraction (SPF) and an insoluble protein fraction. Centrifugation can separate insoluble filamentous proteins and cellular debris from a soluble fraction. Centrifugation can also remove contaminants such as microorganisms. The therapeutic composition is preferably free from insoluble components, as such components are not appropriate for intraperitoneal or sub-cutaneous injection and will not be absorbed and distributed if injected into an animal or human in this manner. Insoluble components can also clog the injection needle during injection. In an embodiment, the homogenate is centrifuged at 15,000 rpm for about ten to about fifteen minutes to provide the soluble fraction and the insoluble fraction. The soluble fraction can be freeze-dried and maintained at about −80° C. under nitrogen.

In an embodiment, the soluble protein fraction is freeze-dried and maintained at about −80° C. under nitrogen. The freeze-dried soluble fraction can be analyzed to determine a ratio of the concentration of soluble protein to lipids. In an embodiment, the powdered soluble fraction includes about 87% soluble proteins and about 13% lipids. If the powdered soluble fraction includes less than about 13% lipids, the powdered soluble fraction can be supplemented with lipids from an additional lipid fraction to achieve a soluble protein fraction having about 87% soluble proteins and about 13% lipids. The additional lipid fraction can be obtained from the freeze-dried EGS, as described herein. The therapeutic composition can include the soluble protein fraction having about 87% soluble proteins and about 13% lipids. The soluble fraction (SPF) (also referred to herein as "Fraction B") can be freeze-dried and stored at about −80° C. under nitrogen.

According to an embodiment, an additional soluble protein fraction can be separated from the insoluble fraction obtained from centrifugation. According to an embodiment, an insoluble fraction obtained from centrifugation in one fractionating cycle can be further fractionated in a subsequent fractionating cycle to provide yet another soluble protein fraction. According to an embodiment, the method can include about two to about four fractionating cycles of insoluble protein fractions, thereby providing a plurality of additional soluble protein fractions. The plurality of additional soluble protein fractions can be pooled and added to the original SPF obtained from the original fractionation of the EGS. The soluble protein fraction (SPF) or "Fraction B" can include the pooled soluble protein fractions. The SPF can be used for IP injection in an animal or human for therapeutic purposes, e.g., to treat diabetes. The SPF (Fraction B) can include lipids as well as soluble proteins (about 87% soluble proteins and about 13% lipids).

The concentration of lipids in the soluble protein fraction can be determined, e.g., by extracting the lipids from a freeze-dried soluble protein fraction and weighing the extracted lipids. If the soluble protein fraction includes about 87% soluble proteins, but less than about 13% lipids, additional lipids can be extracted directly from an EGS and added to the freeze-dried soluble protein fraction to increase the lipid percentage to about 13%. The additional lipids can be extracted from the freeze-dried original EGS. As described in detail, below, lipid extraction can be carried out in the dark and the extracted lipids can be stored under nitrogen until added to the soluble protein fraction. The lipids can be added with an organic solvent, e.g., isopropyl alcohol, to the freeze-dried soluble protein fraction to increase the lipid concentration to about 13% of the total soluble protein-lipid fraction. The organic solvent can be evaporated under vacuum at room temperature.

In an embodiment, if it is determined that the soluble protein fraction includes about 87% soluble proteins but less than about 13% lipids (which is generally the case), additional lipids can be provided by extracting lipids from the EGS with an organic solvent mixture. The additional lipids can be obtained from the freeze-dried EGS by extracting the lipids with an organic solvent mixture including chloroform:methanol:isopropanol (2:1:0.250, v/v) for about 72 hours on a stirring plate. The extracted lipids can then be obtained by filtration, e.g., using a vacuum pump and a Buchner funnel. The lipid extracts can be concentrated to dryness on a rotary evaporator at about 25° C. in the dark and weighed to ensure that the required weight of lipids to be added to the soluble protein fraction is achieved. The required amount of lipids can be dissolved in a suitable organic solvent, e.g., isopropyl alcohol, and added to the soluble freeze-dried protein fraction to increase the lipid fraction in the soluble protein fraction to about 13% of the combined weight of the proteins and lipids. The organic solvent can be evaporated under vacuum at room temperature in the dark to provide a freeze dried soluble protein fraction having about 87% soluble proteins and about 13% lipids of the total combined soluble proteins and lipids. The freeze dried soluble protein fraction (soluble proteins combined with the lipids) can be stored under nitrogen at about −80° C. until needed for injection. The freeze dried soluble fraction can be maintained at about −80° C. (deep freeze) for long-term storage to prevent any unwanted chemical reaction. The enzymes in the fraction will not react against the components in the fraction if kept at about −80° C. during storing for lengthy periods of time under nitrogen. Also the lipids in the soluble protein fraction will be protected from decomposition if kept the same way in deep freeze until required for use. Nitrogen will not allow aerial oxygen to react with the lipids. The SPF is preferably stored in portions appropriate for a single injection at −80° C. It can then be thawed, kept in ice, and administered as needed.

The composition including the SPF (Fraction B) can be administered to a patient to treat diabetes, kidney failure (nephropathy), liver cirrhosis, heart failure, nervous diseases, neuropathy, retinopathy, cancer, and/or fertility problems. The therapeutic composition can be administered to a patient in need thereof, preferably by intraperitoneal (IP) or sub-cutaneous (SC) injection after dissolution in saline, phosphate buffered saline, or other delivery system, such as nanotechnology delivery systems. The therapeutic composition can be combined with a pharmaceutically acceptable carrier. The therapeutic composition can be administered using other delivery methods, e.g., oral administration, provided that the composition is protected from the digestive effects of the elementary canal for oral administration, such as by encapsulation or nano-particle technology. Prior to injection of the soluble protein fraction, the freeze-dried soluble fraction can be dissolved in saline or phosphate buffered saline.

The following examples illustrate the present teachings.

EXAMPLE 1

Preparation of SPF and Calculation of Soluble Protein in Solution

EGS was collected from the catfish skin and kept at −80° C. until use. Frozen EGS was thawed to 4° C., mixed with an equal volume of extraction buffer [phosphate buffered saline (PBS), 0.05 M containing ($NaH_2PO_4/Na_2HPO_4$) and 0.14 M NaCl, pH 7.5], and homogenized with an Ultra Truex (IKA) homogenizer. This step and all subsequent purification procedures were carried out at 4'C unless otherwise indicated. The homogenate was centrifuged at 15,000 rpm for 15 min. The supernatant was collected, and the pellet (insoluble protein fraction) was extracted with extraction buffer (2-4 times for any undissolved soluble compositions). Each time, the soluble fraction was separated from the insoluble fraction by centrifugation as described above, the extracted soluble fractions were pooled. The combined extracted soluble fractions provided the soluble protein fraction (SPF) (Fraction B).

To find the concentration of catfish soluble proteins in the SPF (Fraction B), the SPF was diluted with PBS (1:50). 0.1 ml of the diluted sample was mixed well with 5 ml of Coomassie Brilliant Blue solution and kept in tubes at room temperature for about 10 minutes. Absorbance was read at 595 nm for the sample, and its protein concentration was determined by comparing its absorbance against absorbance for a standard curve for different bovine serum albumin concentrations. Fraction B was found to include about 87% soluble proteins and about 13% lipids.

The SPF (Fraction B) was then dissolved in the extraction buffer for injection.

It is to be understood that the method for preparing a therapeutic composition using epidermal gel secretion of catfish is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method for preparing a therapeutic composition adapted for administration to a patient in need thereof by intraperitoneal (IP) or sub-cutaneous (SC) injection, the method consisting of:

collecting epidermal gel secretions of an Arabian Gulf catfish;

fractionating the epidermal gel secretions to provide a soluble protein fraction and an insoluble protein fraction, the fractionation comprising:

mixing the epidermal gel secretions with an extraction buffer to provide an extract, wherein the extraction buffer includes 0.05 M phosphate buffered saline, pH 7.5 containing 0.14 M NaCl;

homogenizing the extract with a homogenizer to provide a homogenate; and centrifuging the homogenate to provide the soluble fraction and the insoluble fraction, wherein the centrifugation was at 15,000 rpm for 15 minutes, the therapeutic composition comprising the soluble fraction without any insoluble filamentous proteins, cellular debris and microorganisms;

freeze-drying the soluble fraction;

determining whether the freeze-dried soluble fraction includes 87% soluble proteins and 13% lipids; and if the freeze-dried soluble fraction includes less than 13% lipids, supplementing the freeze-dried soluble fraction with a lipid fraction extracted from the epidermal gel secretions of the catfish to obtain a therapeutic composition containing 87% soluble proteins and 13% lipids;

freeze-drying the therapeutic composition containing 87% soluble proteins and 13% lipids; and dissolving the therapeutic composition containing 87% soluble proteins and 13% lipids in saline for administration by intraperitoneal or subcutaneous injection.

* * * * *